United States Patent [19]

Nottbohm

[11] Patent Number: 4,604,088
[45] Date of Patent: Aug. 5, 1986

[54] INSTRUMENT FOR INDIRECT TREATMENT WITH A HOT AIR FLOW AND MOXA SMOKE

[76] Inventor: Friedrich Nottbohm, Am Reisenbrook 24 a, D-2000 Hamburg 67, Fed. Rep. of Germany

[21] Appl. No.: 592,558

[22] Filed: Mar. 23, 1984

[30] Foreign Application Priority Data

Jun. 25, 1983 [EP] European Pat. Off. ........ 83106228.6
Sep. 15, 1983 [DE] Fed. Rep. of Germany ....... 3333271

[51] Int. Cl.$^4$ ............................................. A61B 17/36
[52] U.S. Cl. ....................................... 604/24; 131/175
[58] Field of Search ................ 128/399, 400; 131/175, 131/181; 604/24

[56] References Cited

U.S. PATENT DOCUMENTS

| | | | |
|---|---|---|---|
| 561,288 | 6/1896 | Sondheim | 131/181 |
| 1,457,154 | 5/1923 | Erskine | 131/175 |
| 1,817,823 | 8/1931 | Ito | 604/24 |
| 2,454,631 | 11/1948 | Chneerson et al. | 131/175 |
| 2,561,626 | 7/1951 | Hutcheson | 131/175 |
| 2,625,163 | 1/1953 | Jones et al. | 131/175 |
| 3,100,493 | 8/1963 | Rundle | 131/175 |
| 3,946,733 | 3/1976 | Han | 604/24 |
| 4,203,438 | 5/1980 | Shiu | 604/24 |

FOREIGN PATENT DOCUMENTS

| | | | |
|---|---|---|---|
| 260715 | 1/1965 | Australia | 131/175 |
| 1970085 | 10/1967 | Fed. Rep. of Germany . | |
| 2700920 | 7/1978 | Fed. Rep. of Germany | 131/175 |
| 2917426 | 11/1980 | Fed. Rep. of Germany | 128/399 |
| 8121305 | 12/1981 | Fed. Rep. of Germany . | |
| 624952 | 7/1927 | France . | |
| 9573 | 2/1899 | Sweden | 131/175 |

*Primary Examiner*—Anton O. Oechsle
*Attorney, Agent, or Firm*—Charles W. Helzer

[57] ABSTRACT

The hitherto known indirect moxing instruments are relatively difficult to handle, so that they are frequently not used. This problem is eliminated by the present invention, which provides an instrument which can be easily and rapidly applied by self-therapy to even difficultly reachable points of the body and which ensures optimum effectiveness. Reference is made to the main claim and FIG. 1.

6 Claims, 4 Drawing Figures

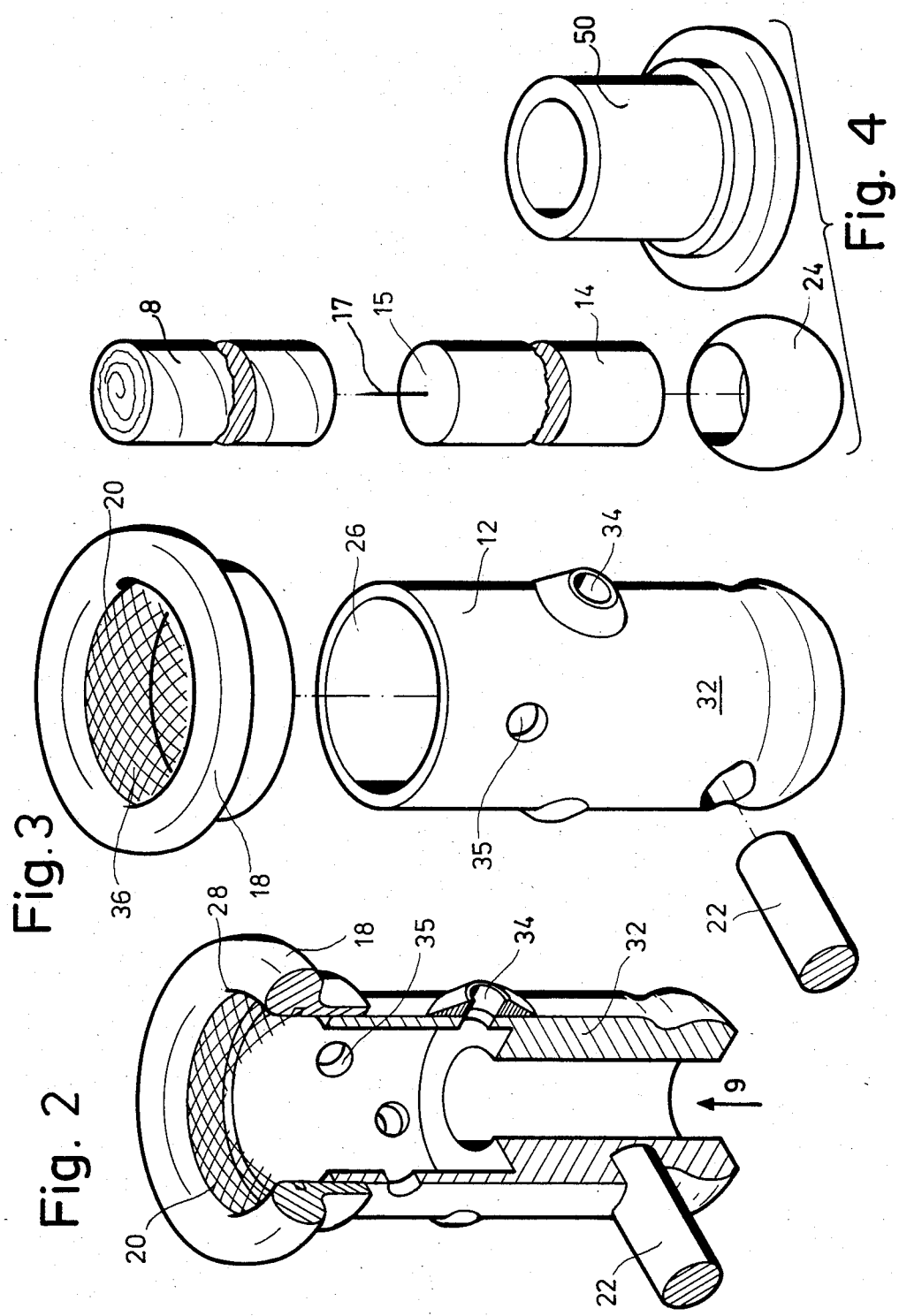

INSTRUMENT FOR INDIRECT TREATMENT WITH A HOT AIR FLOW AND MOXA SMOKE

BACKGROUND OF THE INVENTION

The present invention relates to an instrument for indirect treatment with a hot air flow and moxa smoke according to the preamble of the main claim.

An instrument of this type is, for example, described in the book by August Brodde entitled "Brennen mit Moxakraut", WBV Biologisch-Medizinische Verlagsgesellschaft mbH and Co., KG., 1st edition, 1981, p. 47. This describes the oriental process of moxa smoke application using a tobacco pipe for smoking purposes. The mouthpiece is removed and its joining piece is sealed on to the pipe bowl by means of a candle composition or putty. In the direction of a diagonal through the pipe bowl, a bore is externally made. According to the process described in the above book, a dose of moxa powder is placed in the pipe bowl angle facing the mouthpiece, it is ignited with a taper and with pursed lips an air flow is blown over the glowing moxa powder, so that it passes out of the bore together with the hot moxa smoke. If the pipe is held close to the skin, there is an intense sensation of heat which can be varied by varying the distance between the pipe and the skin. It is immediately apparent that such an instrument is primitive and is also uncomfortable and difficult to use.

SUMMARY OF THE INVENTION

The problem of the present invention is therefore to so improve the aforementioned instrument, that it is easy, safe and fast to use for self application and simultaneously offers a high degree of therapeutic effectiveness.

A further object of the invention is to be able to individually control the heat tolerance of the skin, so that each individual person obtains the optimum utilization of the smoke action in the given unit of time. In addition, the instrument must be simple and inexpensive to manufacture, so as to permit mass production.

The aforementioned problems and objectives are achieved by the instrument characterized in the claims.

The instrument according to the invention, which can also be called a moxer, now makes it possible for the first time to direct the glowing moxa smoke on to the skin in the desired way. The invention is firstly based on the use of a so-called moxa cigar, which can be introduced into the smoke chamber, where it develops its smoke action, in the quantity necesseary for therapy and can subsequently be further inserted. It can be moved axially up and down in the smoke chamber, so that the heat applied to the skin of the user is regulated in the desired manner and the glow can be kept at the desired distance from the skin. According to the invention, a protective grid is provided, so that the moxa ash does not fall directly on to the skin and is instead held back in the grid.

Moxing takes place in the following way. The instrument or moxer according to the invention is held with its cap on the skin of the person to be treated. He can apply the instrument to several points of the body as a result of the long handle provided on the instrument. The skin is subject to the action of the moxa glow smoke through the protective grid of the cap and is heated. Heat accumulation takes place over the skin, which soon can no longer be tolerated by the latter, the heat tolerance of the skin having been reached. The instrument can now be slightly raised (1 to 2 cm) and then lowered again on to the skin. The hot smoke thereby escapes to the outside to a greater extent, so that the skin tolerates the heat again. On relowering the instrument on to the skin, there is a further heat accumulation, which can only inadequately escape via the smoke chamber openings and only completely escapes when the instrument is raised again. The heat can naturally also be controlled in that the moxa glow is brought to a varying distance from the skin moving a plunger rod which holds the moxa cigar and moves it up and down. Heat tolerance is only very briefly extended and the upper tolerance range is largely maintained, an optimum utilization of the smoke action in the given unit of time can be achieved. When the heat evolution intensity subsides, generally after 3 to 5 minutes, the moxa ash must be carefully scraped off and then the glow can be seen again. For this purpose the moxa cigar while mounted on the plunger rod is made removable along with the rod. In other words, the precise fitting opening in the upper region of the smoke chamber makes it possible to readjust the distance between the moxa glow and the protective grid.

Further advantages and features of the invention can be gathered from the subclaims, which can all be of significance to the present invention.

BRIEF DESCRIPTION OF THE DRAWINGS

The invention is described in greater detail hereinafter relative to a non-limitative embodiment and with reference to the attached drawings, which show:

FIG. 2 a perspective partial view of the instrument shown in FIG. 1, in which the smoke chamber is partly shown in section, to permit a better examination of its interior.

FIG. 3 an exploded representation of the previous view.

FIG. 4 a perspective view of the loose plunger rod the end of which includes a moxa cigar holder.

DETAILED DESCRIPTION OF THE INVENTION

Figure 1:
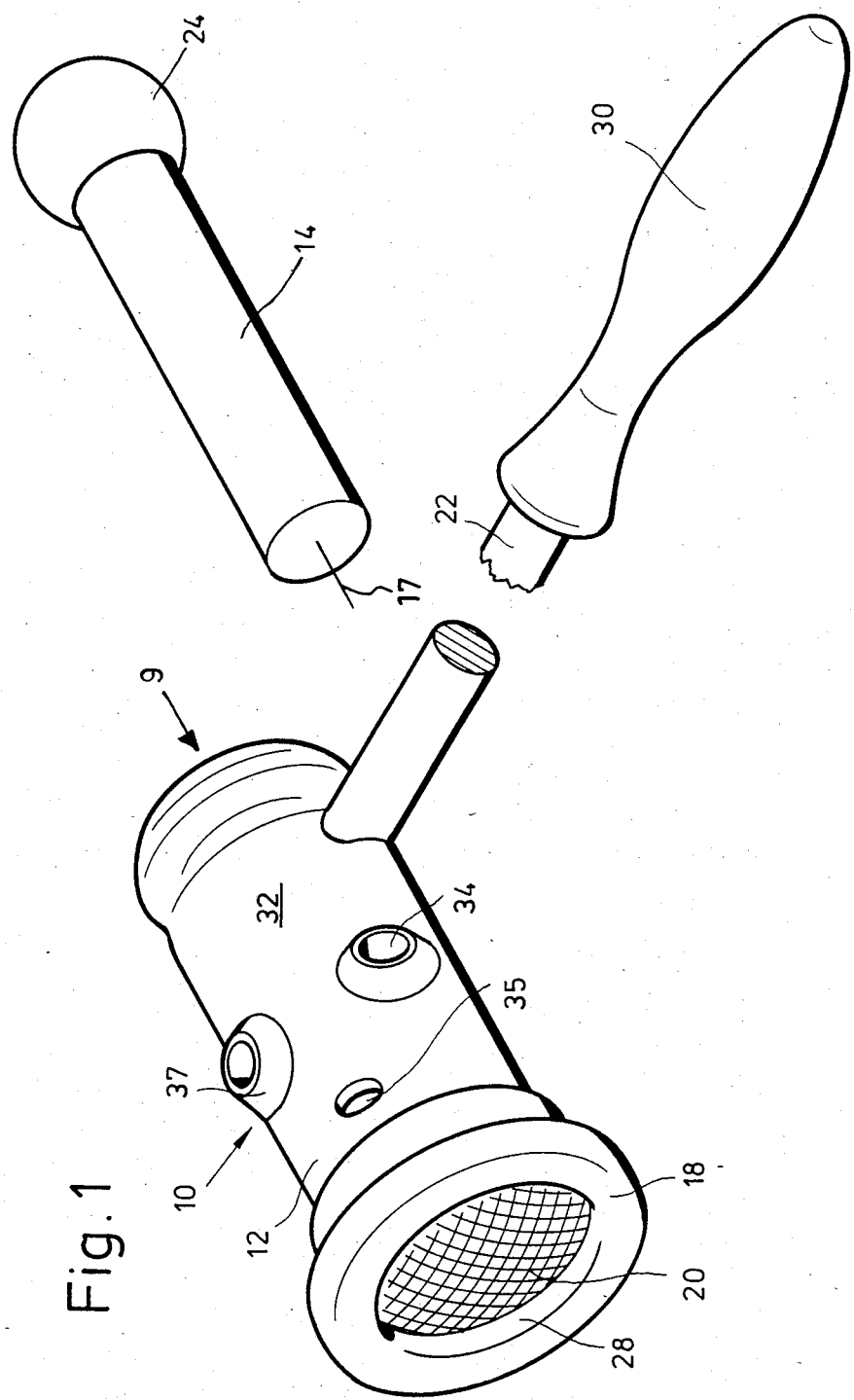
FIG. 1 a perspective view of the instrument according to the invention.

FIG. 1 shows the instrument according to the invention for indirect treatment with hot air flow and moxa smoke for self-therapy in the case of various chronic pain problems particularly those of the head and back. It is shown lying on its side and covered by the general reference 10. It has an approximately cylindrical smoke chamber 12, into which a moxa cigar 8 can be inserted in the use state through a precise fitting opening 9 formed at one end of chamber 12, as best shown in FIG. 2, where it can be moved up and down. A plunger rod 14 having a press fit in opening 9 preferably is used for inserting the cigar. One end of plunger 14 is constructed as a knob 14, whilst its opposite end carries a pin 17 for securement to one end of the moxa cigar 8. The user of the instrument according to the invention can therefore insert the lit and burning end of moxa cigar 8 axially into the smoke chamber (with or without the aid of plunger rod 14). The drawings clearly show that a cap 18 having a relatively close-mesh protective grid 20 removably secured over the opposite end of smoke chamber 12 by a press fit as shown in FIG. 2. To be able to easily and rapidly handle the instrument 10 according to the invention, i.e. to place it on a desired area of the skin of the body of the user with the burning moxa cigar in smoke chamber 12 and cap 18 in place, a long handle in the form of a rod 22 is provided. Rod 22 is inserted and fixed in the solid part 32 of the smoke chamber body 12. The other end of rod 22 has a handle 30.

Smoke chamber 12 is linked with the ambient air by means of a plurality of openings 34, 35, circumferentially arranged around the body of smoke chamber 12 because the open end 9 and cap end 18 which supply the smoke chamber with the oxygen necessary for burning the moxa herb. Externally each of the openings 34 has a surrounding projection 37, which brings about a chimney effect and improves the drawing action.

In the present embodiment, smoke chamber 12, cap 18 and outlets 26, 36 have a circular cross-sectional configuration. In the preferred construction of the invention the cap 18 has an outer edge 28 with a smooth outwardly convex surface configuration so that it can comfortably be applied to the skin of a user. According to the invention, the protective grid 10 is fixed at a certain distance from the lower opening 26 of smoke chamber 12. For this purpose grid 20, is inserted into a circumferential gap in the inner surface cap edge 28 and is made from a thin circular metal wire. Cap 18 is removable, to make it possible to clean the interior of the smoke chamber and also remove ash from the front of the cigar. However, in use, cap 18 is fixed to smoke chamber 12.

In conclusion, a few general comments are made on the moxa herb and moxing with the instrument according to the invention. Moxa herb is the stored, dried common mugwort (herba artemiseae capillaris), which is mainly grown in Asia. Moxa herb has been used in traditional Chinese medicine for many thousands of years particularly in pain therapy. The moxa herb was also a popular herbal medicine in Europe in the 17th and 18th centuries, but has been forgotten as a result of developments in modern medicine.

The term moxing is best defined by heating, smoke application and burning. The healing action of moxing is not so much due to energetic heat application, but to a specific action inherent in the moxa herb. Direct moxing is used to the greatest extent in traditional Chinese medicine, i.e. the moxa herb is burned directly on the skin. Although this constitutes very effective therapy, it is very painful for the patient and can leave behind ugly burns. This type of moxa therapy is generally only carried out by a few specially trained therapists. The moxa therapy developed by Dr. Nottbohm is a so-called indirect process which, by means of the moxer developed by him, hot smoke of the glowing moxa acts on clearly defined skin areas within given units of time. The advantage of indirect moxing is that it is possible to control the smoke action yourself in accordance with the heat tolerance, so as to avoid burns. Indirect moxing is easy to use and can be carried out by anybody after instruction. It is a much safer process and its therapeutic effectiveness is in no way inferior to the direct method.

It has proved advantageous for the protective grid 20 to have openings of approximately 1.6×1.6 mm, the wire being made from vanadium steel with a cross-section of 0.2 mm. This leads to a particularly good guidance and distribution of the hot air flow.

Having described one embodiment of an improved indirect moxer constructed according to the invention, it is believed obvious that other modifications and variations of the invention will be suggested to those skilled in the art in the light of the above teachings. It is therefore to be understood that changes may be made in the particular embodiment of the invention described which are within the full intended scope of the invention as defined by the appended claims.

What is claimed is:

1. An instrument for the indirect self-treatment of chronic pain problems by humans with a hot mixture of air and moxa smoke, particularly head and back pains, said instrument comprising a hollow smoke chamber for receiving a moxa herb rolled in the form of a cigar and having a central opening provided in one end thereof through which it is possible to insert the moxa cigar into the smoke chamber together with means for holding the moxa cigar in the smoke chamber in a precise fitting manner, the opposite end of the smoke chamber having an enlarged opening therein closed by a removable cap which has a protective grid, said smoke chamber having a plurality of further openings around the periphery thereof between the two said ends for the supply of combustion air to the moxa cigar while burning, and a handle secured to the smoke chamber to facilitate handling of the instrument while it is hot during treatment, and wherein the means for holding the moxa cigar in the first mentioned central opening within the hollow smoke chamber in a precise fitting manner comprises a removable and slidable elongated plunger rod forming a press fit with said first mentioned central opening and having a pin formed on the end thereof for attaching and securing the end of a moxa cigar thereto for insertion of the moxa cigar with its opposite free end lit and burning into the hollow interior of the smoke chamber via the first mentioned central opening and for retention of the burning free end of the moxa cigar at a set safe distance from the protective grid.

2. An instrument according to claim 1 wherein the smoke chamber is generally cylindrical in configuration with a generally circular cross-section and wherein the removable cap has a generally smooth convex exterior bead-like surface formed around its outer edge for comfortable contact with the skin of a patient-user and is firmly secured by a press fit to the said opposite end of the hollow smoke chamber.

3. An instrument according to claim 1 wherein the protective grid is secured to the interior of the removable cap at a predetermined safe distance from the bead-like outer edge of the removable cap so that moxa ash caught by the protective grid and the protective grid is prevented from contacting the skin of a patient-user.

4. An instrument according to claim 2 wherein the protective grid is secured to the interior of the removable cap at a predetermined safe distance from the bead-like outer edge of the removable cap so that moxa ash caught by the protective grid and the protective grid is prevented from contacting the skin of a patient-user.

5. An instrument according to claim 4 wherein at least some of the plurality of further apertures around the periphery of the smoke chamber between the ends thereof have projections formed therearound which act as chimneys to provide positive air flow through the smoke chamber and thereby assure good combustion of the burning end of a moxa cigar.

6. An instrument according to claim 1 wherein at least some of the plurality of further apertures around the periphery of the smoke chamber between the ends thereof have projections formed therearound which act as chimneys to provide positive air flow through the smoke chamber and thereby assure good combustion of the burning end of a moxa cigar.

* * * * *